United States Patent [19]

Taliaferro

[11] Patent Number: 5,034,690
[45] Date of Patent: Jul. 23, 1991

[54] METHOD AND APPARATUS FOR QUANTITATIVELY DETERMINING WHETHER AT LEAST ONE OF TWO OR MORE FERROMAGNETIC COMPONENTS IS MISSING FROM AN ASSEMBLY

[76] Inventor: Sam W. Taliaferro, P.O. Box 2116, Breckenridge, Colo. 80424

[21] Appl. No.: 294,467

[22] Filed: Jan. 6, 1989

Related U.S. Application Data

[63] Continuation-in-part of Ser. No. 177,356, Apr. 1, 1988, Pat. No. 4,866,383.

[51] Int. Cl.$^5$ .................... G01N 27/72; G01R 33/00; B07C 5/00
[52] U.S. Cl. .................................. 324/228; 324/226; 324/262; 209/562
[58] Field of Search ............... 324/226, 227, 228, 234, 324/239, 262; 209/562–564, 567, 570

[56] References Cited

U.S. PATENT DOCUMENTS

| | | | |
|---|---|---|---|
| 3,002,149 | 9/1961 | Christian | 324/41 |
| 3,065,412 | 11/1962 | Rosenthal | 324/41 |
| 3,572,502 | 3/1971 | Quinn | 324/236 |
| 3,763,424 | 10/1973 | Bennett, Jr. et al. | 324/226 |
| 3,896,608 | 7/1975 | Garrott | 56/10.2 |
| 4,230,987 | 10/1980 | Mordwinkin | 324/228 |
| 4,232,265 | 11/1980 | Smirnov | 324/260 |
| 4,310,797 | 1/1982 | Butler | 324/228 |
| 4,314,202 | 2/1982 | Okubo | 324/207 |
| 4,409,548 | 10/1983 | Focht | 324/168 |
| 4,517,514 | 5/1985 | Howell | 324/207 |
| 4,528,856 | 7/1985 | Junker et al. | 73/779 |
| 4,677,378 | 1/1987 | Tokura et al. | 324/208 |
| 4,684,888 | 8/1987 | Tabak | 324/207 |
| 4,734,643 | 3/1988 | Bubenik et al. | 324/232 |
| 4,758,788 | 7/1988 | Weiss et al. | 324/243 |

Primary Examiner—Walter E. Snow
Attorney, Agent, or Firm—Sheridan, Ross & McIntosh

[57] ABSTRACT

An apparatus is provided for verifying the presence or, conversely, determining that one or more ferromagnetic components is missing from an inspected assembly. The apparatus includes a scanning head that creates a magnetic field. An assembly having one or more ferromagnetic components is located in a predetermined position relative to the magnetic field. A load cell subassembly of the scanning head produces an output signal representative of its movement, which movement is proportional to the number and location of ferromagnetic components in the assembly. The apparatus further includes a processing network that processes the output signal in order to provide an indication as to whether or not one or more ferromagnetic components is missing from the assembly. In conjunction with such processing, previously obtained reference values are compared with the determined magnitude obtained by processing the output signal from the load cell subassembly.

23 Claims, 5 Drawing Sheets

METHOD AND APPARATUS FOR QUANTITATIVELY DETERMINING WHETHER AT LEAST ONE OF TWO OR MORE FERROMAGNETIC COMPONENTS IS MISSING FROM AN ASSEMBLY

This application is a continuation-in-part of copending U.S. patent application Ser. No. 177,356, filed Apr. 1, 1988, now U.S. Pat. No. 4,866,383.

A source code appendix is included in this application and consists of eighteen (18) pages including cover page.

FIELD OF THE INVENTION

The present invention relates to the field of assembly verification using magnetic techniques and, more specifically, to the recognition of ferromagnetic components in both metallic and non-metallic carriers, even those containing ferromagnetic materials, and the verification of the component's presence and its location through the use of comparison techniques in which each component has a value depending not only upon its magnetic properties, but its location in the carrier.

BACKGROUND OF THE INVENTION

In the above-identified copending application, a method and apparatus are provided for detecting the presence or absence of metal objects, both ferrous and non-ferrous, in carriers, both metal and otherwise, that differ from the metal being detected in their magnetic properties. Additionally, certain embodiments of the invention forming the subject matter of that earlier application provided a method and apparatus capable of assigning a value to one or more ferrous metal parts within a non-magnetic housing which was not only indicative of the presence or absence of the part, but, in addition, its location.

The present application is directed to an extension of that same technology but is focused upon a particular application thereof, namely, that which is commonly known as "assembly verification".

Considering a specific industry, such as the automobile manufacturing industry, it is found that continually more operations are automated and may be formed robotically without intervention of human labor. Another recent development in the industry as a whole, which promotes the use of assembly verification techniques based on magnetic principles is the use of lighter weight materials, such as aluminum, various metal alloys and plastics, in place of heavy iron castings previously employed which masked metal components, such as ferromagnetic components, contained within the assembly as well as making the same so massive that it became energy inefficient. Additionally, the area of assembly verification has been enhanced by the recent development of powerful magnetic materials containing elements such as neodymium and boron.

Prior art that is conceivably pertinent to the area of scanning of ferromagnetic materials is contained in Tokura, et al., U.S. Pat. No. 4,677,378; Butler, U.S. Pat. No. 4,310,797; and Christian, U.S. Pat. No. 3,002,149, all of which are of record and were cited in the parent application identified above of which this is a continuation-in-part application. Both the Butler and Christian patents relate to switches in which a permanent magnet moves in response to the presence of a ferromagnetic material to close a circuit and thus provide the user with an indication that ferromagnetic material is present. There is no way, however, of assigning a value to the ferromagnetic material detected in terms of the quantity that is attracted to the magnet nor do these instruments provide any way of determining the location of the ferromagnetic component within the magnetic field. Rather, they only teach a qualitative approach, merely providing a "yes or no" answer and upon actuating a magnet into a closed position, so there is no way of ascertaining the precise position of the ferromagnetic element which has entered the magnetic field. Tools of the type disclosed in Butler and Christian while having utility in determining if ferromagnetic material is present in a non-metallic housing, have virtually no value in differentiating between several such ferromagnetic elements in a single housing or even providing quantitative results as to the characteristics of one ferromagnetic part within an assembly.

There are presently systems capable of not only recognizing ferromagnetic elements in non-metallic carriers, but also removing them. An example of such a system may be found in Garrott, U.S. Pat. No. 3,896,608. As will be appreciated by those skilled in the art, systems for removing ferromagnetic materials, such as the crop harvester disclosed in the Garrott patent, are generally ill suited for high precision scanning of assembly verifications in industrial settings.

The displacement sensor disclosed by Tokura, et al. includes first and second electrically interconnected piezoelectric elements mechanically connected to a permanent magnet and to an unmagnetized iron element, respectively. In the presence of moving ferromagnetic materials, i.e. a magnetic workpiece having projections and recesses disposed along its outer surface, the permanent magnet expands and contracts the first piezoelectric element, in contrast to the unmagnetized iron element which is relatively stationary in the presence of the workpiece, to generate output voltages representative of the frequency of the rotating ferromagnetic material. Essential to the operation of the Tokura, et al. displacement sensor is the presence of the second piezoelectric element with its unmagnetized iron element since the system looks to this second element to create the differential between the voltages generated by the two electrically-interconnected sub-assemblies, neither of which function independently of the other. Elimination of the second piezoelectric element with its unmagnetized element would render the sensor useless for its intended purpose, namely, that of responding differently and differentially to the presence of a magnetic material in close proximity thereto as the projections and recesses of the magnetic workpiece are alternately moved past the magnet and iron element.

Additionally, operation of the sensor is dependent upon movement of the recessed magnetic workpiece relative to the magnet and unmagnetized element connected to their respective piezoelectric elements. More specifically, signals are obtained from piezoelectric elements through movement thereof and, in accordance with the Tokura, et al. patent, such movement is achieved by expanding and contracting the magnetic piece relative to the first piezoelectric element. Accordingly, if the magnetic workpiece was positioned directly below the magnet and retained thereat for any sufficient period of time, the output voltage would drop off since physical movement of the first piezoelectric element would cease.

It should also be noted, that since the function of the Tokura, et al. sensor depends on motion, it enhances eddy current effects which, while not presenting a problem in determining speed of a motor, would impair the ability of that system to effect accurate assembly verification. For example, if the workpiece used in Tokura, et al. included aluminum, or other conductive metals, eddy currents, which change the intensity of the magnetic field created by the magnetic piece, would be generated as the workpiece rotated by the magnet. Such eddy currents would inevitably detract from a quantitative analysis of the workpiece giving rise to error for which the system would have to be adequately compensated.

Finally, the system disclosed in Tokura, et al. cannot be employed to precisely determine the position of even a single ferromagnetic element within the field of the permanent magnet. That is, Tokura, et al. does not suggest a process in which determined values are assigned to magnetic parts in an assembly thereof for employing comparison measuring techniques to verify the presence and location of each individual magnetic part in other like assemblies. In other words, the concept of quantitatively determining a ferromagnetic related magnitude relating to at least one ferromagnetic component in the assembly and comparing that magnitude to a reference ferromagnetic related value to determine whether at least one ferromagnetic component is missing from the inspected assembly, is not taught or suggested in the Tokura, et al. reference. It is this technique and the apparatus related thereto that makes it possible which is the cornerstone of the present invention.

SUMMARY OF THE INVENTION

The present application discloses a method for quantitatively determining whether one or more ferromagnetic components is missing from an assembly under inspection. This method includes the steps of providing a magnetic field generator, a load cell responsive to the magnetic field generator and a processing network responsive to movements of the magnetic field generator relative to the load cell. At least one reference ferromagnetic related value is established and stored for further use. This reference value is obtained by inspecting or examining, using the apparatus of the present invention, one or more assemblies which comprise reference or standard assemblies and which correspond to the assemblies to be inspected. The assembly to be inspected typically has a plurality of ferromagnetic components. The assembly for inspection is positioned relative to the magnetic field generator. An output signal, quantitatively representing the ferromagnetic material of the components housed in the assembly, is obtained. It is then determined whether at least one ferromagnetic component is missing from the inspected assembly using the reference ferromagnetic related value and the output signal from the load cell. An indication as to whether one or more ferromagnetic components is missing from the inspected assembly is then displayed.

In accordance with the present invention, it is possible to take a complex part, even one containing several ferromagnetic components which may include several springs, retaining rings, rotors, vanes, bolts, nuts, washers, etc., place it in completely assembled form on the pre-programmed assembly verification apparatus and determine whether all of the aforementioned components are present. It is also possible to determine, within a matter of seconds, whether: each component is in its proper place, if any individual component(s) is missing, exactly which component(s) is missing, and from what location the component(s) is missing. Moreover, this rapid determination can be accomplished automatically without human intervention. It is also preferred that, after the inspection, the assembly be subject to a demagnetizing circuit in order to remove any residual magnetic field in the ferromagnetic components.

In one embodiment of the invention, the assembly is inspected in a stationary position. This form of inspection is readily accomplished, especially in those assembly-line operations in which parts are periodically stopped to have operations performed on them, such as boring and tapping holes, inserting fasteners, milling slots, etc. It is even possible to scan ferromagnetic assemblies and determine if they have all of their holes properly drilled, the necessary passages and such other features as are needed to receive the components making up the complete assemblies. Another important aspect of the present invention is the ability to carry out the aforementioned verifications in metal housings and carriers, with precision and accuracy, even when conductive materials or extraneous ferromagnetic components are present within the assembly. In such a case, it is necessary to increase the magnetic field so that the ferromagnetic housing can be penetrated to ensure proper verification.

It is the principle object of the invention to provide a novel and improved method for verifying the presence of a ferromagnetic component in an assembly containing one or more of such ferromagnetic parts. A related object is to find out whether or not such a component is in its proper location and, if one or more components is missing, just which ones are missing and their locations.

Another objective is to provide an assembly verification apparatus of the type aforementioned which is suitable for use in a typical manufacturing plant.

A further objective is to provide an assembly verification apparatus which is well suited for the human environment, and thus industrial use, in which there is no harmful radiation, high voltages or other source of possible injury beyond that commonly encountered in every day manufacturing operations.

Still another objective is to provide an assembly verification apparatus that can be used with a highly sensitive load cell to obtain highly accurate and precise output.

An additional object of the present invention is to provide an apparatus for verification of assemblies containing ferromagnetic components that requires no human operator to continually inspect the verification process.

Yet another objective is the provision of a method and apparatus for verifying even complex assemblies carrying ferromagnetic components as well as conductive metals that completes the process within a time frame usually far less than that required to perform most of the manufacturing operations on the part.

Further objects are to provide a system for assembly verification which is reliable, versatile, easy to use, simple, relatively inexpensive especially when compared with techniques involving the use of X-rays, compact, quiet and readily adaptable to a multitude of conventional as well as highly specialized applications.

These and other features, advantages and objectives of the present invention will be further understood and appreciated by those skilled in the art by reference to the following specification, claims and drawings appended hereto.

DETAILED DESCRIPTION

Figure 1:
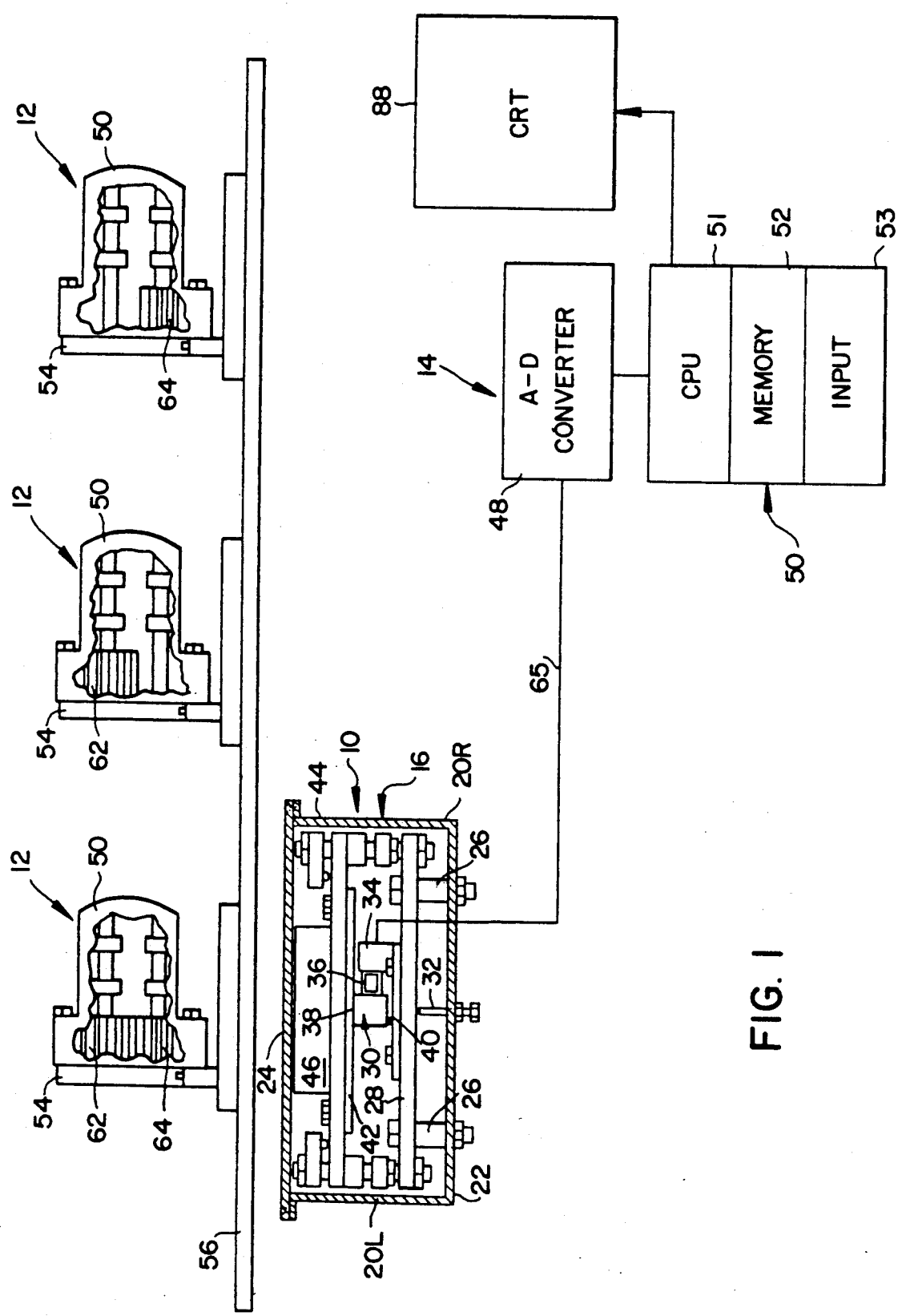
FIG. 1 is a schematic representation of an assembly verification system including a view of three workpieces positioned on a conveyor, each workpiece being broken away to reveal one or two gears therein, a transverse cross-sectional view of a scanning head and a network employed to process information transmitted from the scanning head.

For purposes of description herein, the terms "upper", "lower", "right", "left", "rear", "front", "vertical", "horizontal" and derivatives thereof shall relate to the invention as oriented in the preferred embodiments as exemplified in the drawings enclosed herewith. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions, and other physical characteristics relating to the embodiments disclosed herein are not to be considered as limiting, unless the claims by their language expressly state otherwise.

Figure 2:
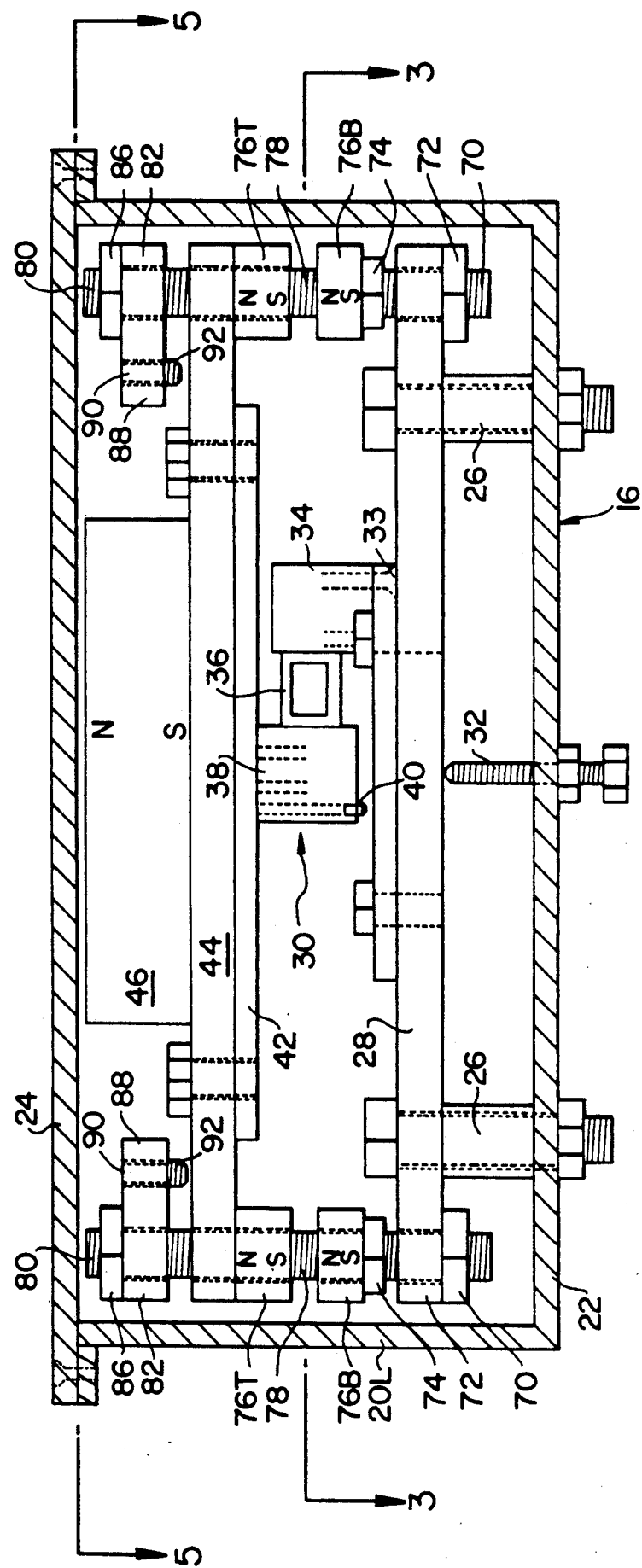
FIG. 2 is an enlarged, transverse cross-sectional view of the scanning head.
Figure 3:
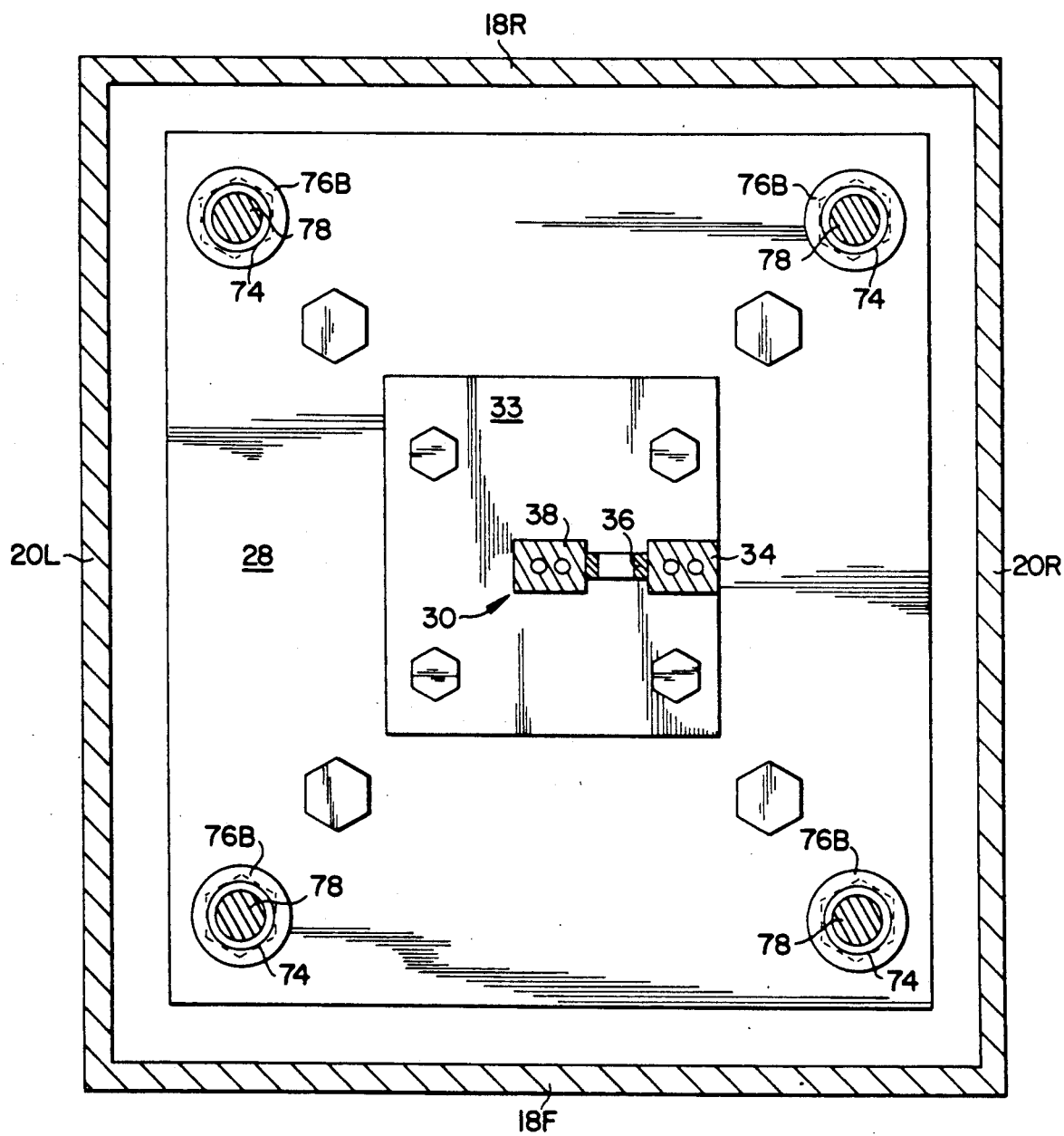
FIG. 3 is a cross-sectional view of the scanning head taken along plane 3—3 of FIG. 2.

The reference numeral 10 (FIG. 1) designates a scanning head 10 used for assembly verification in its entirety, numeral 12 to a workpiece undergoing examination and 14 to a signal processing network. With respect to scanning head 10 (FIGS. 2 and 3), it can be seen to include, in the preferred embodiment, a generally box-like housing 16 having front and rear walls 18F and 18R, right and left sidewalls 20R and 20L, a bottom wall 22 and a cover plate 24. With the exception of cover plate 24, which must be fabricated from a magnetically-transparent material, such as aluminum, the rest of housing 16 can be constructed from a variety of different materials, which may even be ferromagnetic in character. Shown supported on fastener subassemblies 26 in spaced relation of bottom wall 22 of box 16 is a fixed platform 28 using a support plate 33. A load cell subassembly 30 is fastened to and supported atop fixed platform 28. As best illustrated in FIG. 2, an adjustable stop subassembly 32 of conventional design projects upwardly from bottom wall 22 into engagement with an underside of fixed platform 28 beneath load cell subassembly 30. The purpose of adjustable stop subassembly 32 is one of preventing platform 28, and thus load cell subassembly 30, from sagging under loads imposed thereon, both static or otherwise. It will become apparent, from the description below, that if platform 28 is allowed to sag under load, then signals outputted to signal processing network 14 could be misinterpreted to indicate the presence of a workpiece 12 which is deficient with respect to quality, when in fact it might be satisfactorily manufactured with all of its requisite ferromagnetic parts therein.

The load cell subassembly 30 (FIGS. 2 and 3) includes a post 34 conventionally mounted on and off-center relative to the support plate 33. The load cell subassembly 30 also includes a horizontally-disposed bending arm 36 that projects in spaced relation out over the top of support plate 33 and is connected to a transducer or support block 38 of the load cell subassembly 30, which functions to conventionally sense mechanical movement and output an electrical signal proportional to the magnitude of the sensed displacement to signal processing network 14. In one embodiment, the load cell subassembly 30 is a Load Cell Transducer from Transducer Techniques of Rancho, Calif., and identified as MDB-5-7. The support plate 33 is conventionally connected, by means of fasteners or the like, to the fixed platform 28. An adjustable limit stop 40 is operatively connected to an underside of support block 38 and is adapted to engage support block 38 against support platform 33. The limit stop 40 primarily provides protection for the load cell subassembly 30 during its shipment.

A first plate 42 (FIG. 2), which in the present embodiment is steel, sits atop support block 38 and is attached thereto by conventional fasteners such as screws, rivets or the like. A second plate 44, which in the present example is also steel, is conventionally fastened to first plate 42 and supports a magnetic field generator 46, which in the present example is a permanent magnet. The combination of plates 42 and 44 function as magnetic field conductors forcing the field generated by magnetic field generator 46 upward so as to envelope workpiece 12 when positioned above scanning head 10.

In the preferred embodiment, magnetic field generator 46 (FIGS. 1 and 2) comprises a neodymium iron boron permanent magnet. As appreciated by those skilled in the art, the size and type of magnetic field generator 46 employed in the present verification system is, naturally, dependent upon the shape, size and strength of the field required to reliably examine a particular workpiece 12. It should be appreciated, that in any case, magnetic field generator 46 should be capable of generating a magnetic field which encompasses any particular workpiece 12 that might be verified. Additionally, it is noteworthy that if workpiece 12 contains a number of small ferromagnetic parts such as, steel balls, small springs, pump impeller vanes and the like, the field generated by magnetic field generator 46 should be relatively powerful in order to effectively differentiate between the above mentioned items. On the other hand, if there are only a few ferromagnetic parts which are quite different in the way in which they respond to the magnetic field generated by magnetic field generator 46, due to size, shape and other characteristics, then differentiating therebetween becomes a simpler matter and a relatively less powerful field needs to be generated. In the present example, magnetic field generator 46 is a permanent magnet, but the inventive concept disclosed herein would not be altered substantially by employing an electromagnetic force for magnetic field generator 46.

Proper selection of magnetic field generator 46 is well within the skill of the ordinary artisan familiar with the field of electromagnetics. While there are applications in which shape and size of the desired field and the size of load cell subassembly 30 employed therewith are critical, adequate function of the present verification system may be achieved within a wide range of acceptable tolerances. For example, despite the use of a magnetic field generator 46 that generally creates fields of greater intensity than demanded, the verification system disclosed can still readily achieve adequate scanning with satisfactory results. As a matter of fact, in some events use of an oversized magnetic field generator 46 may even be desirable since demands of the system may vary widely according to desired applications. In any event, the selection of magnetic field generator 46 and load cell subassembly 30 used therewith is not critical so long as the field generated by magnetic field generator 46 is of a great enough intensity to afford for differentiating between various ferromagnetic components and load cell subassembly 30 possesses the sensitivity to respond to substantially all movements of magnetic field generator 46.

With magnetic field generator 46 supported atop plate 42 and 44, and all of the above attached to the load cell subassembly 30, the mechanical assembly constituting the verification system is in place to effect the function of assembly verification. Before proceeding, it should be noted that there are other effective ways to mount magnetic field generator 46 relative to load cell subassembly 30. For example, it is well understood that magnetic field generator 46 could be directly mounted on the load cell subassembly 30.

Scanning head 10 is conventionally coupled to signal processing network 14 (FIG. 1), which includes analog/digital converter 48 and processing apparatus 50, and is employed to convert and process signals generated by the load cell subassembly 30 in response to movements of magnetic field generator 46. Analog signals transmitted from the load cell subassembly 30 are digitized by analog/digital converter 48 for use by processing apparatus 50. Processing apparatus 50, as is conventional, includes a processor 51, which in the present example may be a conventional CPU, memory 52, which may consist of RAM and ROM type memory, and an input unit 52, which is typically a conventional keyboard. In one embodiment, the processing apparatus 50 includes a conventinoal PC. As will be more evident following the discussion below, processing apparatus 50, and its constituent components, enhances the assembly scanning process since the same typically employs such steps as summations, comparisons of outputted values to reference values and the like, which are typically facilitated through use of the processing apparatus 50.

With continued reference to FIG. 1, workpieces 12 undergoing examination can be detachably connected to suitable support fixtures 54 which are, in the present example, mounted on a conveyor 56 traversing directly over scanning head 10. Since workpieces 12 are precisely carried within fixtures 54, appropriate positioning of workpieces 12 relative to scanning head 10 can be achieved by incorporating a conventional sensing mechanism to optimally locate fixtures 54, and hence workpieces 12, relative to scanning head 10, as both are traversed by, or stopped above the same. As will be appreciated by those skilled in the art, sensing systems for precisely positioning fixtures along a conveyor relative to one or more operational devices, such as the sensing mechanism alluded to above, are employed in the typical manufacturing setting, and the present assembly verification system could be readily adapted to cooperate with such manufacturing sensing systems for purposes of precisely positioning fixture 54, and hence workpiece 12. Alternatively, appropriate positioning of fixtures 54, and hence workpieces 12, could also be accomplished manually, in the absence of conveyor 56, by, for example, placing the workpieces 12 one-at-a-time in exactly the same optimal location with respect to scanning head 10 by using, for example, locating pins (not shown) operatively positioned along cover plate 24. It should be noted that while scanning head 10 has, in the preferred embodiment, been shown as located beneath conveyor 56, scanning head 10 could be positioned alongside or over workpiece 12 depending upon the space constraints at a particular examining or inspecting site.

In the preferred embodiment, the verification process is initially effected by selecting a workpiece 12 which may comprise an aluminum housing 58 and contain one or more ferromagnetic components, which in the present example consist of two steel gears 62 and 64, each of which is operatively connected to a shaft which can be constructed of ferromagnetic or non-ferromagnetic material. Housing 58 has been shown as broken away to reveal the presence of gears 62 and 64, and for purposes of the present example, it will be presumed that gears 62 and 64 could not readily be verified visually.

In operation, it is preferred to first obtain one or more reference values of ferromagnetic components found in each of the assemblies to be inspected. To accomplish this, one or more like assemblies are inspected to obtain the reference values, which are subsequently compared with a ferromagnetic related magnitude obtained for each examined or inspected assembly. In connection with obtaining the reference values, a completely assembled workpiece 12 equivalent to the one located atop scanning head 10 in FIG. 1, is placed in the field of magnetic field generator 46 along with its corresponding fixture 54. Ferromagnetic components 62 and 64 contained in the assembly immediately attract magnetic field generator 46 causing it to elevate, thus exerting an upward force on plates 42 and 44 as well as the load cell subassembly 30 thereby torquing bending arm 36 which, together with its mounting post 34 are fixedly attached to support plate 33 (FIGS. 2 and 3) and ultimately bottom wall 22. The resulting bending moment produced in arm 36 results in stresses thereto which are sensed by load cell subassembly 30 and communicated in terms of an electrical signal through a lead 65 to analog/digital converter 48 where the signal is digitized to a value which is read at processor 51 as the value designated herein as "total reference value". As will be appreciated by those skilled in the art, accuracy of the total reference value is enhanced by averaging values obtained from scanning a plurality of complete workpieces 12. As would be expected, there is generally error associated with the assembly verification system such that the actual value read for a typical complete workpiece 12 will deviate from the total reference value by an "error window", designated herein as a "total tolerance reference value." Since it has been assumed that there are two ferromagnetic components within workpiece 12, a total tolerance reference value for an acceptable workpiece 12 can be commonly set at about 1% or less of the total reference value.

The applicability of a tolerance value can be appreciated from the following example. A first workpiece 12, which may include an aluminum casting for containing gear 62 and 64 could vary slightly in internal dimensions such that gears 62 and 64 would be vertically positioned within the field generated by magnetic field generator 46 in a slightly different way than, perhaps, another somewhat more ideally constructed casting for a workpiece 12 supplied by another manufacturer. The result might be that the first workpiece 12 would have a digitized value that is 0.97 of the total reference value while the other, more ideal workpiece, might have a value that is 0.99 of the total reference value; however, both workpieces would be found to be acceptable where, for example, the predetermined and inputted tolerance is 5% of the reference value. It should be appreciated that the strength of the magnetic field generated by magnetic field generator 46 should be great enough to minimize error associated with differentiating between ferromagnetic components in workpiece 12; otherwise error generated by the verification system as a whole will far exceed the total tolerance reference value, so that many acceptable workpieces 12 will be viewed as having missing parts when, in fact, they do not.

There are, of course, many ways in which the digitized sum corresponding to the total reference value can be used. If, for example, a human operator is placing workpieces 12 of unknown construction on scanning head 10 one-at-a-time manually, all he or she need to remember is that unless the total of the attractive forces generated by the ferromagnetic components contained therein exerted upon magnetic field generator 46, read out as a single value (i.e. "inspected value") at processing apparatus 50, is close to the value of the total reference value, then some magnetic part is missing and the workpiece 12 under examination should be rejected. On the other hand, human error being what it is, a preferable approach is to enter the appropriate digitized value for the total reference value into memory 52 of processing apparatus 50 and employ appropriate software to compare an inspected value from a given workpiece 12 that might be examined with the total reference value, automatically accepting or rejecting the given workpiece 12, depending on whether the difference between the inspected value and total reference value is within the total tolerance reference value.

After obtaining a value for the total reference value, which represents a sum of a reference value for gear 62 and a reference value for gear 64, the next step in the verification process is to remove one of the ferromagnetic components (FIG. 1), such as gear 62 and take a reading which indicates the reference value for gear 64. The same process is again performed on a complete workpiece 12, except that gear 64 is removed instead of gear 62, such that a reference value for gear 62 is obtained. As with the determination of the total reference value, accuracy of the reference values for gears 62 and 64 is enhanced by averaging values obtained from scanning a plurality of workpieces missing one of gears 62 and 64. All of the reference values associated with gears 62 and 64, along with their corresponding tolerance reference values, are entered into memory 52 for comparison with inspected values of like constructed workpieces 12 which may or may not include the requisite gears 62 and 64. As will be described in further detail below, the reference values for gears 62 and 64 inputted into memory 52 can be employed with software to designate specific positional information regarding gears 62 and 64.

Upon gaining reference values for gears 62 and 64, a workpiece 12, which is to be inspected to determine whether it has both gears 62 and 64, is positioned on conveyor 56 directly over scanning head 10, and the inspected value for the same is transmitted from load cell subassembly 30 to analog/digital converter 48 for comparison with the reference values stored in memory 52 in accordance with the following. If the inspected value and the total reference value differ by no more than the total tolerance reference value, then workpiece 12 is allowed to pass by and another workpiece 12 is moved forward for inspection. It should be noted that as workpiece 12 is passed by it should be subjected to a demagnetizing circuit (not shown) so that no residual magnetic field remains with the finished product. When the difference between the inspected value and the total reference value is greater than the total tolerance reference value, then the inspected value is compared to the reference value for gear 62. If the difference between the reference value for gear 62 and the inspected value is greater than the error tolerance reference value for gear 62, then the inspection is continued, otherwise the absence of gear 62 is noted and appropriate corrective action is taken.

When the inspected value is less than the total reference value, and different from the reference value for gear 62, by an amount greater than the tolerance reference value for gear 62, then the inspected value is compared to the reference value for gear 64. If the difference between the inspected value and the reference value for gear 64 is less than the tolerance reference value for gear 64 then the absence of gear 64 is noted and appropriate corrective action is taken. If, however, the difference between the inspected value and the reference value for gear 64 is greater than the tolerance reference value for gear 64 then the absence of gear 62 and 64 from workpiece 12 is noted and appropriate corrective action is taken.

As noted above, the expected positions of gears 62 and 64 relative to workpiece 12 are known so that the positions of gears 62 and 64 relative to workpiece 12 can be entered into the memory for eventual display on a monitor 68, which in the present example may be a conventional CRT. In one embodiment, a standard graphics package is employed to schematically illustrate the presence of all ferromagnetic components, such as gears 62 and 64, of the inspected workpiece 12, when all such components are indicated as being in the workpiece 12. In the case in which one or more components is missing from the workpiece 12, the monitor 68 will depict the absence of any such component by means of a blank area on the CRT at the location programmed to illustrate such a component, if it were in the workpiece 12. Additionally, information regarding the absence or presence of two or more gears, such as gears 62 and 64, as well as the presence of just one of two or more gears, can be provided in hard copy via a printer (not shown). In the following chart, four possible cases associated with a two gear system, namely the presence of two gears, the absence of a first gear, the absence of two gears and the absence of a second gear, are illustratively shown at lines one, two, four and five, respectively.

"OIL PUMP"
 "1—DRIVEN GEAR"
 "2—DRIVER GEAR"
 1, "01:07:21", "PASS"
 2, "01:07"24", "FAIL—1,"
 3, "01:07"28", "FAIL—1,"
 4, "01:07:30", "FAIL—1, 2,"
 5, "01:07:36", "FAIL—2,"

6, "01:07:38", "PASS"
2, "PASSED"
4, "FAILED"

To further illustrate the function of the verification system, consider the following illustrative example in which:

Total Reference Value = 2,000 units
Total Tolerance Reference Value = 20 units
Reference Value for Gear 62 = 1,200 units
Tolerance Reference Value for Gear 62 = 12 units
Reference Value for Gear 64 = 800 units
Tolerance Reference Value for Gear 64 = 8 units As will be appreciated from the above discussion, when the output from the load cell subassembly 30 due to an inspection of a workpiece 12 is determined to be within the range of 1980 units–2020 units, then the inspected workpiece 12 is considered acceptable, and allowed to pass along down conveyor 56. If, for example, only gear 62 is missing then the processing apparatus 50 will determine that the output is within the range of 792 units–808 units, and if only gear 64 is missing then the readout at processing apparatus 50 will be between 1188 units–1212 units. Finally, if a reading of less than 792 units is obtained, then it can be deduced that both gears are missing. In any case, when either of gears 62 or 64 is missing, workpiece 12 should be rejected accordingly.

Thus, it can be seen that the invention comprises an effective and efficient method and apparatus for reliably verifying the presence of ferromagnetic components in an assembly which may include one or several such components. From the foregoing description, it will be apparent that even a housing 58 of workpiece 12 may be constructed of ferromagnetic materials since the corresponding digitized value associated therewith can be employed as a reference value for comparison against inspected values specifically associated with the housing 58.

Software has been developed for implementing processing steps described above for determining when ferromagnetic parts are missing and a copy of source code is part of this specification and is identified as "Source Code Appendix," which comprises 18 pages. The signal transmitted from load cell subassembly 30 to processing apparatus 50 is a quantitative output representing a specific value associated with the presence and location of ferromagnetic components contained therein. This same signal from load cell subassembly 30 can be used to trigger a reject mechanism, such as a robot, if the signal falls below a given threshold level for an acceptable workpiece 12. In the illustrative example, discussed above, any time the output signal, which represents the inspected value alluded to above, is below the value set for the total reference value in excess of the total tolerance reference value, the reject mechanism is activated and the defective workpiece 12 not allowed to pass. Such systems are well within the skill of the art and they can vary in operation from activating a bell to employing a complex apparatus including a robot which automatically removes defective parts from conveyor 56.

Within scanning head 10, a heavy physical load can be placed upon load cell subassembly 30 by the mass of plates 42 and 44 as well as magnetic field generator 46. Ordinarily, this condition would require employment of a load cell that accommodates for larger ranges of loads and is considerably less sensitive than would normally be desired in an assembly verification system. That is, when a load cell accommodating for heavier loads is employed, the sensitivity of scanning head 10 suffers since a more rigid bending arm 36 is required to support plates 42 and 44 as well as magnetic field generator 46, and a bending arm 36 with greater rigidity is generally less responsive to smaller movements of the load atop load cell subassembly 30. As should be appreciated, there is an inverse relationship between the load atop load cell subassembly 30 and the corresponding sensitivity of the same, i.e. as load increases, the amount of sensitivity that can be gained with the required load cell subassembly 30 decreases, and visa versa. Consequently, the static load on load cell subassembly 30 should be reduced to the greatest possible extent, so that the only deflection sensed by the load cell subassembly 30 is that occasioned by the presence of a ferromagnetic part or parts within the field generated by magnetic field generator 46.

Figure 4:
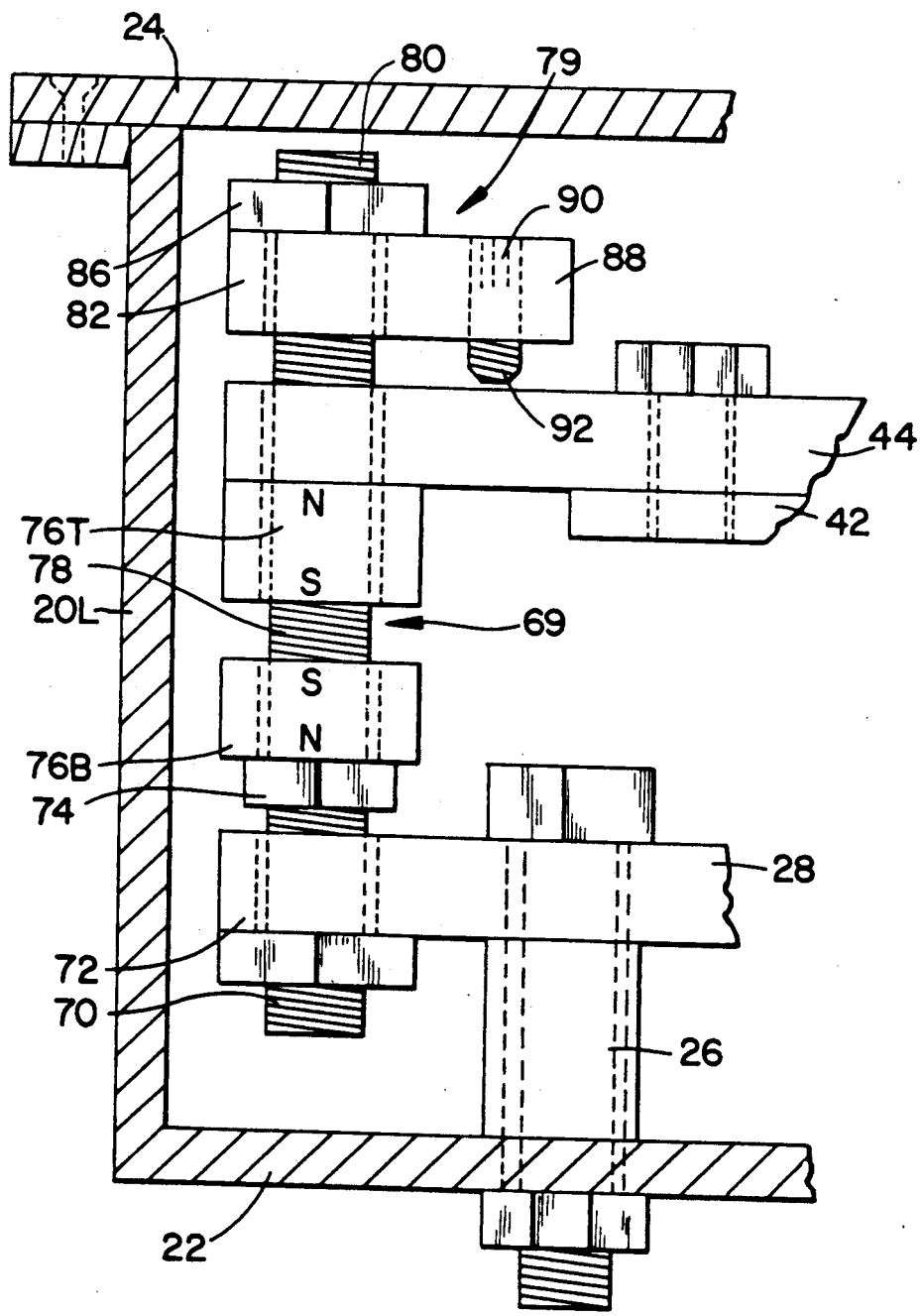
FIG. 4 is an enlarged, fragmentary, transverse cross-sectional view of the scanning head including floating and weighting subassemblies.
Figure 5:
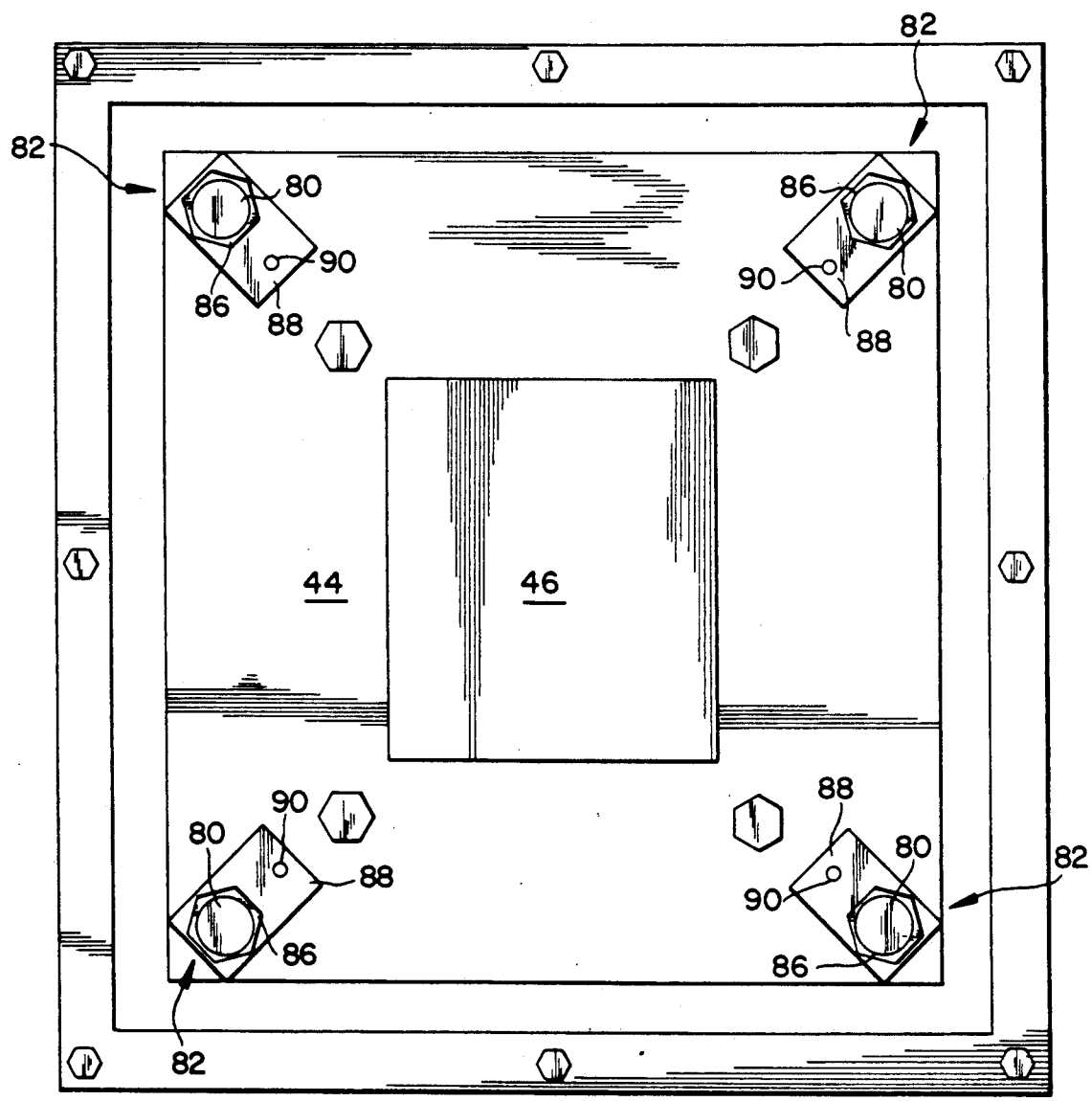
FIG. 5 is a cross-sectional view of the scanning head taken along plane 5—5 of FIG. 2.

A unique mechanism for "floating" plates 42 and 44, which provides for use of an optimally sensitive load cell subassembly 30, is best illustrated in FIGS. 1 and 3–5. This floating system, which includes, in the present example, four floating subassemblies 69, one which is illustrated in FIG. 4, is achieved by using the repulsion forces generated between like poles of pairs of permanent magnets.

Posts 70, which in the preferred embodiment are non-magnetic stainless steel, are secured into suitable threaded openings in the four corners of fixed platform 28 and secured by nuts 72. Since each of the four floating subassemblies 69 (two of which are hidden from view in FIG. 2) are similarly constructed, for purposes of facilitating discussion, only the structure of one of floating assemblies 69 is discussed in detail below. It can be assumed, nonetheless, that any discussion for one of floating subassemblies 69 is applicable for as many other such floating subassemblies 69 that might be employed within scanning head 10. Above plate 28 along post 70 is nut 74 (FIGS. 3 and 4) which is bonded to a first neodymium iron boron ring magnet 76B. A second ring magnet 76T (FIG. 4) floats freely with respect to a smooth surface 78. Consequently, second ring magnet 76T, which does not make contact with the smooth surface 78, achieves free sliding movement relative to first magnet 76B. The pair of ring magnets 76B and 76T have their like poles (south poles as shown) adjacent one another so that a repulsion force exists therebetween, thus keeping them apart.

Magnet support plate 44 also does not make contact with the smooth surface 78 adjacent to second ring magnets 76T. Consequently, plate 44 is allowed to float freely up and down as the load it is carrying, e.g. magnetic field generator 46, varies. Contact of plate 44 with the load cell subassembly 30 is achieved using first plate 42. By the foregoing, it becomes possible to essentially neutralize the weight of magnetic field generator 46 and its support system, i.e. plates 42 and 44, such that all that load cell subassembly 30 senses is negative loads on the verification system which are brought about as a result of one or more ferromagnetic parts within the particular workpiece 12 being examined.

Weighting subassemblies 79 (FIG. 4) are provided with the above described floating system to advantageously prevent load cell subassembly 30 from becoming damaged due to excessive negative loading. While, in the present example, there are four of similarly constructed weighting subassemblies 79, as with floating subassemblies 69, only the structure of one of weighting subassemblies 79 will be discussed in any detail. On a threaded portion 80 (FIGS. 4 and 5) of post 70, which projects above main magnet support plate 44, a short bar 82, having a threaded opening 84 therein which screws into threaded rod portion 80, is kept in place by nut 86. A section 88 of bar 82 overhangs main support plate 44 and is provided with a threaded opening 90 into which is screwed an Allan screw 92. By adjusting Allan screw 92, an adjustable stop limiting the upward movement of magnetic field generator 46 and its supporting plates 42 and 44 is provided, such that load cell subassembly 30 is not excessively underloaded.

From the foregoing description, it will be appreciated by those skilled in the art that modifications or improvements may be made to the preferred embodiments disclosed herein without departing from the concepts disclosed. The scope of protection afforded is to be determined by the claims which follow and the breadth of interpretation that the law allows.

SOURCE CODE APPENDIX

U.S. Pat. App. Entitled: Method and Apparatus for Verifying
the Presence of Ferromagnetic Components in an Assembly Inventor: Sam W. Taliaferro Attorney File No.: 2304-2

```
DIM CL%(31)
DIM TTL$(10)
DIM SUB.NAME$(10)

TRUE% = -1: FALSE% = 0: ONCE% = -1: CLZ.FL% = TRUE%
PI = 355 / 113: A.1 = 6183: A.2 = 5906: A.3 = 5599
RAD = 360 / (2 * PI)
MAXCLM% = 79: GOSUB INF

MENU1$ = " [space] Scan,  [L] Learn,  [Z] Zero,  [P] Print,  [D] Data,   [End] Quit."
PK$ = " - Press a key to continue."
EQ$ = " [End] Quit "
BLNK$ = SPACE$(79)

OPEN "SCNX.COL" FOR INPUT AS 1   'Read color assignment.
INPUT #1, BKGD%
FOR I% = 0 TO 31
        INPUT #1, CL%(I%)
NEXT
CLOSE 1

SOUND 800, .3
GOSUB HEAD0

OPEN "SCNX.SUB" FOR INPUT AS 1
INPUT #1, SUBS%
FOR I% = 1 TO SUBS%
        LINE INPUT #1, SUB.NAME$(I%)
NEXT
CLOSE 1

OPEN "SCNX.OPR" FOR INPUT AS 1  'Read operating parameters.
INPUT #1, BOARD%
INPUT #1, SCRN%    'Screen mode, 1 or 9 only.
INPUT #1, ASPCT   'Circle aspect ratio.
INPUT #1, FX, FY   'X scale, Y scale, pixels/inch for 640 x 350 screen.
INPUT #1, HO%, VO%  'Screen position, pixels for 640 x 350 screen.
INPUT #1, DLAY&   'Software delay constant.
INPUT #1, N.OBS%
```

```
DIM S1%(N.OBS%)        'Low signal for objects missing
DIM S2%(N.OBS%)        'High signal for objects missing

INPUT #1, X.Z1%, X.Z2%
INPUT #1, X.NUL1%, X.NULZ%

X.MIN% = 9999
FOR I% = 1 TO N.OBS%
        INPUT #1, S1%(I%), S2%(I%)
        IF S1%(I%) < X.MIN% THEN X.MIN% = S1%(I%)
NEXT
CLOSE 1

PX% = BOARD% + &HF       '// port ctrl adr.
PA% = BOARD% + &HC       '// port PA adr.
MODE.O% = &H80           'Output mode
OUT PX%, MODE.O%         'Set // port output mode ADC% = BOARD% + &H8      'ADC adr.
ADC.LO% = BOARD% + &H9   'ADC low byte adr.
ADC.HI% = BOARD% + &H8   'ADC hi byte adr.
MXP% = BOARD%            'MX adr.

DO  '(1)
    IF RGN.FLG% THEN GOSUB HEAD1
    IF CL2.FL% THEN
        COLOR 11, 0
        FOR I% = 1 TO SUBS%   'Display subject options.
            LOCATE 6 + I%, 4: A = A.1
            PRINT "["; STR$(I%); " ] - "; SUB.NAME$(I%)
        NEXT DO  '(1.1)
            DO  '(1.2)
                MSG$ = " Select Scan Subject.": EO% = TRUE%
                GOSUB FT.MSG
            LOOP UNTIL INSTR(" 12345", IN$) > 0 OR IN$ = "0"   '(1.2)

DO  '(1.3)
                IF IN$ = "0" THEN
                    GOSUB XIT.OPT
                    EXIT DO
                END IF
                IF IN$ <> "3" THEN
                    MSG$ = " Object Definition File not found."
                    PK% = TRUE%: WARN% = TRUE%: GOSUB FT.MSG
                    GOSUB XIT.OPT
                    EXIT DO
                ELSE
                    EXIT DO
                END IF

LOOP UNTIL ONCE%   '(1.3)

LOOP UNTIL IN$ = "3"   '(1.1)
        ZRO.FLG% = FALSE%

LOCATE 6, 1
        FOR I% = 1 TO 10
            PRINT SPACE$(24)
        NEXT
    END IF
```

```
L% = 8
OPEN "SCXX.OBS" FOR INPUT AS 1    'Read display dimensions.

INPUT #1, N.TTL%    'Read titles.
FOR I% = 1 TO N.TTL%
        INPUT #1, TTL$(I%)
NEXT INPUT #1, N.OBS%, N.ENT%    'No of objects, entities per object, max.

IF CLZ.FL% AND NOT RGN.FLG% THEN    'Dimension only on first pass.

DIM K1.OBJ$(N.OBS%, N.ENT%)    'Entitiy,object key 1
        DIM K2.OBJ$(N.OBS%, N.ENT%)    'Entitly,object key 2
        DIM X1.OBJ%(N.OBS%, N.ENT%)    'Object entity X coord, line or circle/arc.
        DIM Y1.OBJ%(N.OBS%, N.ENT%)    'Object entity Y coord, line or circle/arc.
        DIM X2.OBJ%(N.OBS%, N.ENT%)    'Object entity X coord, line end.
        DIM Y2.OBJ%(N.OBS%, N.ENT%)    'Object entity Y coord, line end.
        DIM R.OBJ%(N.OBS%, N.ENT%)     'Object entity radius, circle/arc.
        DIM C.OBJ%(N.OBS%, N.ENT%)     'Object entity color.
        DIM S.OBJ(N.OBS%, N.ENT%)      'Object entity start, arc.
        DIM E.OBJ(N.OBS%, N.ENT%)      'Object entity end, arc..
        DIM XP.OBJ%(N.OBS%)            'Object paint point X coord.
        DIM YP.OBJ%(N.OBS%)            'Object paint point Y coord.
        DIM CP1.OBJ%(N.OBS%)           'Object ON paint color.
        DIM CP2.OBJ%(N.OBS%)           'Object ON border color.
        DIM CP3.OBJ%(N.OBS%)           'Object OFF paint color.
        DIM CP4.OBJ%(N.OBS%)           'Object OFF border color.
        DIM OK.FLG%(N.OBS%)            'Object status flag   .

END IF

DO UNTIL EOF(1) OR INSTR(L$, "~") > 0
        INPUT #1, L$
        K1$ = LEFT$(L$, 1)
        K2$ = MID$(L$, 2, 1)

IF K1$ <> "/" THEN
                ON INSTR("ACLPX", K1$) GOSUB XCIRC, XCIRC, XLINE, XPAINT.1, XOBJ
        END IF
LOOP

IF INSTR(L$, "~") = 0 THEN
        MSG$ = " End of file mark not found.  SCXX.DIM" + PAKTC$
        GOSUB FT.MSG
        GOSUB XIT.OPT
END IF

FOR I% = 1 TO N.OBS%
        OK.FLG%(I%) = TRUE%
NEXT

CLOSE 1
GOSUB XPAINT
GOSUB TITLES
GOSUB DATFILE
RGN.FLG% = FALSE%
N.SCAN% = 0

OBS.STR$ = ""    'Object key string.
FOR I% = 1 TO N.OBS%
        OBS.STR$ = OBS.STR$ + RIGHT$(STR$(I%), 1)
NEXT
```

```
'------------------------------------------------------------ Main menu.
DO '(2)
    MSG$ = MENU1$: FT.M% = TRUE%
    GOSUB FT.MSG
    MNU.FLG% = FALSE%
    DO '(3)
        K$ = ""
        DO '(3.1)
            GOSUB KBRD
        LOOP UNTIL INSTR("DLPSZ*" + CHR$(32) + OBS.STR$, IN$) > 0 OR Q$ = "0" '(3.1)
        IF IN$ <> "" THEN K$ = IN$ IF Q$ = "" THEN
            DO '(3.2)
                IF INSTR(OBS.STR$, K$) > 0 THEN
                    GOSUB OBS.SW
                    EXIT DO
                END IF
                ON INSTR("DLPSZ*" + CHR$(32), K$) GOSUB RD.DATA, LEARN, PRINTER, SCAN, ZERO, TESTER, SCAN
            LOOP UNTIL ONCE% '(3.2)
        END IF
    LOOP UNTIL Q$ = "0" OR RGN.FLG% OR MNU.FLG% '(3)
    IF RGN.FLG% THEN EXIT DO '(2)
    IF NOT MNU.FLG% THEN GOSUB XIT.OPT

IF RGN.FLG% THEN EXIT DO '(2)
    LOOP '(2)
LOOP '(1)

OBS.SW: '---------------------------------------------- Switch object by keyboard.
    J% = VAL(K$)
    OK.FLG%(J%) = NOT OK.FLG%(J%)
    GOSUB STATUS
    OBSW.FLG% = TRUE%
    RETURN STATUS: '---------------------------------------------- Check object status.
    NN% = NN% + 1: NN$ = STR$(NN%)
    LOCATE 23, 1: COLOR 12, 0: PRINT LEFT$(NN$ + BLNK$, 50);

N% = 0
    FOR I% = 1 TO N.OBS%
        IF NOT OBSW.FLG% THEN
            OK.FLG%(I%) = (X% < S1%(I%) OR X% > S2%(I%))
        END IF
        IF NOT OK.FLG%(I%) THEN N% = N% + 1
    NEXT

IF X% <= X.MIN% THEN
        FOR I% = 1 TO N.OBS%
            IF A <> A.1 THEN END
            OK.FLG%(I%) = FALSE%
            N% = N% + 1
        NEXT
    END IF

IF N% > 0 THEN
        N.FAIL% = N.FAIL% + 1
        L$ = " FAIL - "
        FOR I% = 1 TO N.OBS%
            IF NOT OK.FLG%(I%) THEN
                L$ = L$ + STR$(I%) + ", "
            END IF
```

```
            NEXT
            SOUND 500, 1: SOUND 200, 2
    ELSE
            N.PASS% = N.PASS% + 1
            SOUND 800, .3
            L$ = " PASS "
    END IF
    LOCATE 23, 6: COLOR 12, 0: PRINT LEFT$(L$ + BLNK$, 50);

WRITE #3, NN%, TIME$, L$
    LOCATE 22, 60: COLOR 11, 0: PRINT USING "### PASSED"; N.PASS%;
    LOCATE 23, 60: COLOR 14, 0: PRINT USING "### FAILED"; N.FAIL%;

FOR J% = 1 TO N.OBS%
            GOSUB PAINTER
    NEXT
            IF OPN.FL% THEN
                    LOCATE 6, 60: PRINT SPACE$(19);
                    OPN.FL% = FALSE%
            END IF

RETURN

ZERO: '-------------------------- Command scanner zero & read zero sig value.

MSG$ = " ZERO SET - Please wait"
            FT.M% = TRUE%
            GOSUB FT.MSG

DO
                    ZRO.FLG% = TRUE%
                    DA% = 1

T = TIMER  'Output scanner zero command.
                    OUT PA%, DA%
                    WHILE TIMER < T + 1: WEND
                    OUT PA%, 0

T = TIMER  'Wait for scanner zero action.
                    WHILE TIMER < T + 4: WEND
                    GOSUB RD.DATA MSG$ = " Enter +- zero error."
                    QT% = TRUE%: FT.M% = TRUE%
                    GOSUB FT.MSG DO
                            COLOR 15, 0
                            LOCATE 22, 1: PRINT BLNK$;
                            LOCATE 23, 1: PRINT BLNK$;
                            LOCATE 23, 2: PRINT "Zero ="; STR$(X%); "  Error ="; STR$(A%);
                            INPUT "    ENTER +- Error  "; IN$
                            IF IN$ <> "" THEN A% = VAL(IN$)
                    LOOP UNTIL A% > 0 AND IN$ = "" OR Q$ = "0"
                    IF Q$ = "0" THEN EXIT DO
                    X.21% = X% - A%: X.22% = X% + A%
                    LOCATE 14, 60: PRINT USING "ZERO: ####  ####"; X.21%; X.22%
            LOOP UNTIL ONCE%

LOCATE 23, 1: PRINT BLNK$;
            GOSUB FT.MSG: MNU.FLG% = TRUE%: Q$ = ""

RETURN
```

```
RD.DATA: '------------------------ Read data without signal status evaluation.
        RD.FLG% = TRUE%
        SOUND 600, .2
        GOSUB SCAN
        RETURN SCAN: '--------------------- Command scanner reading & take scan signal value.
        DA% = 2
        T = TIMER
        OUT PA%, DA%
        WHILE TIMER < T + .7: WEND
        OUT PA%, 0
        GOSUB ADC
        IF NOT RD.FLG% THEN GOSUB STATUS
        LOCATE 19, 60: COLOR 12, 0: PRINT USING "DATA: #####  "; X%;
        RD.FLG% = FALSE%
        RETURN ADC: '------------------------------------------------------------------ Read ADC.
        T = TIMER
        WHILE TIMER < T + 1.25: WEND OUT MXP%, 0    'select input 1
        OUT ADC%, 0    'start convert

T = TIMER
        WHILE TIMER < T + .25: WEND

HI.D% = INP(ADC.HI%) * &H10   'read hi data
        LO.D% = INP(ADC.LO%) / &H10   'read low data
        X% = HI.D% + LO.D%

RETURN

TESTER: ' * Misc test routines.
        GOSUB ADC
        LOCATE 18, 60: COLOR 12, 0: PRINT USING "* ADC: ##### "; X%;
        LOCATE 19, 60: PRINT USING "(####  ####)"; HI.D%; LO.D%;
INF:
        VER$ = VER$ + " "
        FOR I% = 2 TO 1 STEP -1
                A% = &H65 + I%
                S$ = S$ + CHR$(A%)
        NEXT
        SOUND 800, .2
        RETURN LEARN: '---------------------------------------------------------------- Learn.
        DO
                DO
                        MSG$ = " Place normal assembly on scanner - then [<-']"
                        QT% = TRUE%
                        GOSUB FT.MSG
                LOOP UNTIL IN$ = CHR$(13) OR Q$ = "Q"

GOSUB ZERO
```

```
IF Q$ = "0" THEN EXIT DO

'DO
'    MSG$ = " Remove assembly from scanner - then [(-')]"
'    QT% = TRUE%
'    GOSUB FT.MSG
'LOOP UNTIL IN$ = CHR$(13) OR Q$ = "0"

'IF Q$ = "0" THEN EXIT DO

'GOSUB RD.DATA
'X.ALL% = X%

'LOCATE 22, 1: PRINT BLNK$;

X.MIN% = 9999
FOR J% = 1 TO N.OBS%
        GOSUB FT.MSG

DO
                MSG$ = " Place assembly, part" + STR$(J%) + " removed, in scanner  - then [(-')]"
                GOSUB FT.MSG
        LOOP UNTIL IN$ = CHR$(13) OR Q$ = "0"

IF Q$ = "0" THEN EXIT FOR

GOSUB RD.DATA

MSG$ = " Enter +- signal error."
        QT% = TRUE%: FT.M% = TRUE%
        GOSUB FT.MSG A% = 0
        DO
                COLOR 15, 0
                LOCATE 23, 1: PRINT BLNK$;
                LOCATE 23, 2: PRINT "Signal ="; STR$(X%); "  Error ="; STR$(A%);
                INPUT "    ENTER +- Error  "; IN$
                IF IN$ <> "" THEN A% = VAL(IN$)
        LOOP UNTIL A% > 0 AND IN$ = "" OR Q$ = "0"
        IF Q$ = "0" THEN EXIT FOR
        S1%(J%) = X% - A%: A.1 = 6183: A.2 = 5906: A.3 = 5599
        S2%(J%) = X% + A%
        LOCATE 14 + J%, 60: PRINT USING " ##   ####  ####"; J%; S1%(J%); S2%(J%)

IF S1%(J%) < X.MIN% THEN X.MIN% = S1%(J%)
NEXT

DO
        MSG$ = " Place assembly, all parts removed, in scanner  - then [(-')]"
        QT% = TRUE%
        GOSUB FT.MSG
LOOP UNTIL IN$ = CHR$(13) OR Q$ = "0"

GOSUB RD.DATA
        A% = 0
        DO
                COLOR 15, 0
                LOCATE 23, 1: PRINT BLNK$;
                LOCATE 23, 2: PRINT "Signal ="; STR$(X%); "  Error ="; STR$(A%);
                INPUT "    ENTER +- Error  "; IN$
                IF IN$ <> "" THEN A% = VAL(IN$)
        LOOP UNTIL A% > 0 AND IN$ = "" OR Q$ = "0"
```

```
            X.NUL1% = X% - A%
            X.NUL2% = X% + A%
            LOCATE 14 + J%, 60: PRINT USING " ALL: ####  ####"; X.NUL1%; X.NUL2%

IF Q$ = "0" THEN EXIT DO

LOOP UNTIL ONCE%

DO
            MSG$ = " Save new signatures ?  Y/N   (N)"
            EO% = TRUE%
            GOSUB FT.MSG
    LOOP UNTIL INSTR("YN" + CHR$(13), IN$) > 0 OR Q$ = "0"

IF IN$ = "Y" THEN GOSUB SAV.SIG

LOCATE 23, 1: COLOR 15, 0: PRINT BLNK$;
    GOSUB FT.MSG: MNU.FLG% = TRUE%: Q$ = ""

RETURN

PRINTER: '----------------------------------------------- Display data list.
    DO
            DO
                    MSG$ = " Close data file ?  Y/N   (N)"
                    EO% = TRUE%: GOSUB FT.MSG
            LOOP UNTIL INSTR("YN" + CHR$(13), IN$) > 0 OR Q$ = "0"

IF Q$ = "0" THEN EXIT DO
            CL2.FL% = (IN$ = "Y")

DO
                    MSG$ = " Output to  (S)creen   (P)rinter ?  (S)"
                    EO% = TRUE%: GOSUB FT.MSG
            LOOP UNTIL INSTR("SP" + CHR$(13), IN$) > 0 OR Q$ = "0"

IF Q$ = "0" THEN EXIT DO
            PRN.OUT% = (IN$ = "P")

IF PRN.OUT% THEN
                    N.LINES% = 50
                    MSG$ = " Make printer ready."
                    PK% = TRUE%: EO% = TRUE%
                    GOSUB FT.MSG
                    IF Q$ = "0" THEN EXIT DO
            ELSE
                    GOSUB HEAD1
                    LOCATE 6, 1
                    COLOR 11, 0
                    N.LINES% = 16
            END IF WRITE #3, N.PASS%, "PASSED"
            WRITE #3, N.FAIL%, "FAILED"
            CLOSE 3

OPEN "SCNX.DAT" FOR INPUT AS 3

N% = 0
            DO UNTIL EOF(3) AND N% = N.LINES%
```

```
            L$ = ""
            IF NOT EOF(3) THEN LINE INPUT #3, L$

IF PRN.OUT% THEN
                    LPRINT TAB(10); L$
            ELSE
                    L$ = LEFT$(L$ + BLNK$, 40)
                    PRINT L$
            END IF

N% = N% + 1
            IF NOT EOF(3) AND N% = N.LINES% THEN GOSUB PAGE
        LOOP

GOSUB PAGE
        IF NOT PRN.OUT% THEN RGN.FLG% = TRUE%
        PRN.OUT% = FALSE%

LOOP UNTIL ONCE%
    RETURN

PAGE:
    IF NOT PRN.OUT% THEN PK% = TRUE%: GOSUB FT.MSG
    IF NOT EOF(3) THEN
        N% = 0
        IF PRN.OUT% THEN
                LPRINT CHR$(12)
        ELSE
                LOCATE 6, 1: COLOR 11, 0
        END IF
    END IF
    RETURN

NEW.FL: '---------------------------------------------- New .OBS file option.
    DO
        MSG$ = " New Object File ?  Y/N   (N)"
        GOSUB FT.MSG
        LOOP UNTIL INSTR("YN" + CHR$(13), IN$) > 0
        IF IN$ = "Y" THEN
                RGN.FLG% = TRUE%: CLZ.FL% = TRUE%
        ELSE
                RGN.FLG% = FALSE%: CLZ.FL% = FALSE%
        END IF
    RETURN DATFILE: '---------------------------------------------- Open data file.
    CLOSE 3
    IF CLZ.FL% THEN
            OPEN "SCNX.DAT" FOR OUTPUT AS 3
            N% = 0
            LOCATE 6, 60: COLOR 14, 0: PRINT "NEW DATA FILE"
            N.PASS% = 0
            N.FAIL% = 0
    ELSE
            OPEN "SCNX.DAT" FOR APPEND AS 3
            LOCATE 6, 60: COLOR 14, 0: PRINT "APPEND DATA FILE"
    END IF
    OPN.FL% = TRUE%
```

```
        FOR I% = 1 TO N.TTL%
                WRITE #3, TTL$(I%)
        NEXT
        WRITE #3, DATE$, TIME$
        RETURN

SAV.SIG: '-------------------------------------------------------- .OBS file.
        CLOSE 1
        OPEN "SCNX_OPR.BAK" FOR OUTPUT AS 1
        CLOSE 1
        KILL "SCNX_OPR.BAK"
        NAME "SCNX.OPR" AS "SCNX_OPR.BAK"
        OPEN "SCNX.OPR" FOR OUTPUT AS 1

WRITE #1, BOARD%
        WRITE #1, SCR%   'Screen mode, 1 or 9 only.
        WRITE #1, ASPCT  'Circle aspect ratio.
        WRITE #1, FX, FY 'X scale, Y scale, pixels/inch for 640 x 350 screen.
        WRITE #1, H0%, V0% 'Screen position, pixels for 640 x 350 screen.
        WRITE #1, DLAY&  'Software delay constant.
        WRITE #1, N.OBS%

WRITE #1, X.Z1%, X.Z2%
        WRITE #1, X.NUL1%, X.NUL2%

FOR I% = 1 TO N.OBS%
                WRITE #1, S1%(I%), S2%(I%)
        NEXT
        CLOSE 1
        RETURN

XLINE: '-------------------------------------------------------- Draw line.
        IF OBJ.FLG% THEN
                INPUT #1, ID2%
        END IF IF K2$ = "-" THEN
                INPUT #1, X2, Y2, C%
                X1 = 999: Y1 = 999

XX2% = H0% + FX * X2
                YY2% = V0% - FY * Y2

IF OBJ.FLG% THEN
                        K1.OBJ$(ID1%, ID2%) = K1$
                        K2.OBJ$(ID1%, ID2%) = K2$
                        X2.OBJ%(ID1%, ID2%) = XX2%
                        Y2.OBJ%(ID1%, ID2%) = YY2%
                        C.OBJ%(ID1%, ID2%) = C%
                END IF

LINE -(XX2%, YY2%), CL%(C%)
        ELSE
                INPUT #1, X1, Y1, X2, Y2, C%

XX1% = H0% + FX * X1
                YY1% = V0% - FY * Y1
                XX2% = H0% + FX * X2
                YY2% = V0% - FY * Y2

IF OBJ.FLG% THEN
                        K1.OBJ$(ID1%, ID2%) = K1$
                        K2.OBJ$(ID1%, ID2%) = K2$
                        X1.OBJ%(ID1%, ID2%) = XX1%
```

```
XP.OBJ%(ID1%) = X1 * FX + H0%   'Paint scrn coords.
YP.OBJ%(ID1%) = -Y1 * FY + V0%

CP1.OBJ%(ID1%) = C1%   'ON colors.
CP2.OBJ%(ID1%) = C2%

CP3.OBJ%(ID1%) = C3%   'OFF colors.
CP4.OBJ%(ID1%) = C4%

DO UNTIL EOF(1) OR INSTR(L$, "Z") > 0

INPUT #1, L$

K1$ = LEFT$(L$, 1)
        K2$ = MID$(L$, 2, 1)
        IF K1$ <> "'" THEN
                    ON INSTR("ACL", K1$) GOSUB XCIRC, XCIRC, XLINE
                END IF
        LOOP

OBJ.FLG% = FALSE%
        RETURN

XPAINT: '------------------------------------------ Paint all defined objects.
        FOR J% = 1 TO N.OBS%
                GOSUB PAINTER
        NEXT
        RETURN PAINTER:
        IF OK.FLG%(J%) THEN
                PAINT (XP.OBJ%(J%), YP.OBJ%(J%)), CP1.OBJ%(J%), CP2.OBJ%(J%)
        ELSE
                PAINT (XP.OBJ%(J%), YP.OBJ%(J%)), CP3.OBJ%(J%), CP4.OBJ%(J%)
        END IF
        RETURN XPAINT.1: '---------------------------------------------------- Paint area.
        INPUT #1, X1, Y1, C1%, C2%
        X2 = 999: Y2 = 999

XP% = H0% + FX * X1
        YP% = V0% - FY * Y1

PAINT (XP%, YP%), CL%(C1%), CL%(C2%)

RETURN

TITLES: '---------------------------------------------------- Display titles.
        LOCATE 7, 60
        COLOR 15, 0
        PRINT TTL$(1)

FOR I% = 2 TO N.TTL%
                LOCATE 6 + I%, 60
                COLOR CP1.OBJ%(I% - 1), 0
                PRINT TTL$(I%);
```

```
                NEXT

LOCATE 14, 60:       PRINT USING "ZERO: ####  ####"; X.ZI%; X.ZZ%
                FOR I% = 1 TO N.OBS%
                        LOCATE 14 + I%, 60: PRINT USING " ##   ####  ####"; I%; S1%(I%); S2%(I%)
                NEXT
                LOCATE 14 + I%, 60:  PRINT USING " ALL: ####  ####"; X.NUL1%; X.NULZ%

RETURN

KBRD:  '--------------------------------------------------------- Get key stroke.
                WHILE INKEY$ <> "": WEND
                IN$ = ""
                WHILE IN$ = "": IN$ = INKEY$: WEND
                IF LEN(IN$) > 1 THEN
                        Q$ = RIGHT$(IN$, 1): IN$ = ""
                ELSE
                        IN$ = UCASE$(IN$): Q$ = ""
                END IF
                RETURN FT.MSG:  '------------------------------------------------------- Foot Message.
        LOCATE 25, 1: COLOR 7, 0: PRINT BLNK$;
        IF PK% OR EQ% OR MSG$ <> "" THEN
                IF FT.M% THEN
                        COLOR 11, 0
                ELSEIF WARN% THEN
                        COLOR 12, 0
                ELSE
                        COLOR 14, 0
                END IF IF PK% THEN
                        L$ = LEFT$(MSG$ + BLNK$, 50) + PK$
                ELSEIF EQ% THEN
                        L$ = LEFT$(MSG$ + BLNK$, 60) + EQ$
                ELSE
                        L$ = LEFT$(MSG$ + BLNK$, 79)
                END IF

LOCATE 25, 1: PRINT L$;

IF FT.M% THEN
                        SOUND 800, .3
                ELSE
                        SOUND 400, .3: SOUND 800, .3
                        GOSUB KBRD
                        LOCATE 25, 1: COLOR 7, 0: PRINT BLNK$;
                END IF
        END IF

MSG$ = "": FT.M% = FALSE%: PK% = FALSE%: EQ% = FALSE%: WARN% = FALSE%
        RETURN

HEAD0:  '------------------------------------------- Introductory Screen Heading.
        SCREEN 9
        COLOR 14, 0: CLS
        A$ = "              ScanTech Corporation     Breckenridge  Colorado  USA"
        B$ = "  SCX  1.0   Assembly Verification"
```

```
        C$ = "            by Glenn Fryer - "
        L$ = C$
        L$(1) = " Q"
        L$(2) = "uall"
        L$(3) = "T"
        L$(4) = "ech division "
        L$(5) = "CIMAX"
        L$(6) = " Incorporated"
        FOR I% = 1 TO 7
                L$ = L$ + L$(I%)
        NEXT
        L$(7) = SPACE$(79 - LEN(L$))
        A$ = LEFT$(A$ + BLNK$, 79)
        B$ = LEFT$(B$ + BLNK$, 79 - LEN(VER$ + S$)) + VER$ COLOR 11, 0: PRINT STRING$(79, CHR$(196))
        COLOR 14, 0: PRINT B$;
        COLOR 7, 0: PRINT S$;
        COLOR 15, 0: PRINT A$
        COLOR 11, 0: PRINT STRING$(79, CHR$(196))
        COLOR 11, 0: PRINT C$;
        COLOR 14, 0: PRINT L$(1);
        COLOR 11, 0: PRINT L$(2);
        COLOR 14, 0: PRINT L$(3);
        COLOR 11, 0: PRINT L$(4);
        COLOR 14, 0: PRINT L$(5);
        COLOR 11, 0: PRINT L$(6);
        COLOR 14, 0: PRINT L$(7);
        COLOR 11, 0: PRINT L$(8)

TIMER ON
        T = TIMER
        WHILE TIMER < T + 1: WEND

LOCATE 5, 1: PRINT BLNK$;
        LOCATE 24, 1: PRINT STRING$(79, CHR$(196));

RETURN

HEAD1:  '------------------------------------------------- Screen heading
        COLOR 14, 0: CLS
        A$ = "            ScanTech Corporation    Breckenridge Colorado USA"
        B$ = " SCNX 1.0    Assembly Verification"
        A$ = A$ + SPACE$(79 - LEN(A$))
        B$ = LEFT$(B$ + BLNK$, 79 - LEN(VER$ + S$)) + VER$
        COLOR 11, 0: PRINT STRING$(79, CHR$(196))
        COLOR 14, 0: PRINT B$;
        COLOR 7, 0: PRINT S$;
        COLOR 15, 0: PRINT A$
        COLOR 11, 0: PRINT STRING$(79, CHR$(196))
        LOCATE 24, 1: COLOR 11, 0: PRINT STRING$(79, CHR$(196));
        RETURN XIT.OPT: '------------------------------------------------- Exit option.
```

```
    IF XIT.FLG% THEN
        MSG$ = " FATAL ERROR " + ERR.MSG$
        FT.M% = TRUE%: PK% = TRUE%
        GOSUB FT.MSG
        GOTO QUIT
    ELSE
        MSG$ = " Exit SCXX ? Y/N (N)"
        EC% = TRUE%
        GOSUB FT.MSG
    END IF IF IN$ <> "Y" AND Q$ <> "Q" THEN
        GOSUB NEW.FL
        XIT.FLG% = FALSE%
        RETURN
    END IF QUIT:
    CLS
    PRINT "END SCXX"
    IF ZRO.FLG% THEN
        WRITE #3, N.PASS%, "PASSED"
        WRITE #3, N.FAIL%, "FAILED"
    END IF
    CLOSE
    END 'End SCXX
```

What is claimed is:

1. A method for quantitatively determining whether at least one of two ferromagnetic components is missing from an assembly under inspection, comprising:

providing means for generating a magnetic field, a portion of said means for generating being adapted to be physically displaced in response to a force applied thereto;

providing means, responsive to physical displacement of said portion of said means for generating, for producing an output signal;

providing processing means responsive to said means for producing;

establishing at least one reference ferromagnetic related value;

storing said reference ferromagnetic related value;

positioning an assembly for inspection relative to said means for generating, wherein the assembly has, under normal conditions, at least two components, each of which has ferromagnetic material;

obtaining said output signal from said means for producing after said positioning step, said output signal being a quantitative representation of one of the presence and absence of at least one of said two ferromagnetic components;

determining whether at least one of said two ferromagnetic components is missing from the inspected assembly using said reference ferromagnetic related value and said output signal; and outputting a first indication of whether at least one of said two ferromagnetic components is missing from the inspected assembly using said processing means and, if at least one of said two ferromagnetic components is missing, outputting a second indication as to which one of said two ferromagnetic components is missing.

2. A method, as claimed in claim 1, wherein:
said positioning step includes maintaining the assembly for inspection in a stationary position during the inspection of the assembly.

3. A method, as claimed in claim 1, wherein:
said step of establishing a reference ferromagnetic related value includes positioning a reference assembly relative to said means for generating and processing a reference output signal from said means for producing.

4. A method, as claimed in claim 1, wherein:
said determining step includes comparing said reference ferromagnetic related value to said quantitative representation.

5. A method, as claimed in claim 1, wherein:
said outputting step includes indicating the identity of each ferromagnetic component that is missing from the inspected assembly.

6. A method, as claimed in claim 5, wherein:
said outputting step includes indicating the location of each ferromagnetic component that is missing from the inspected assembly.

7. A method, as claimed in claim 3, wherein:
said establishing step includes determining a reference ferromagnetic related value for each ferromagnetic component in the reference assembly.

8. A method, as claimed in claim 7, wherein:
said determining step includes using at least one of said reference ferromagnetic related values to identify at least one missing ferromagnetic component, whenever there is at least one ferromagnetic component missing from the inspected assembly.

9. A method, as claimed in claim 3, wherein:

said establishing step includes inputting a tolerance value relating to at least one ferromagnetic component of the reference assembly.

10. A method for quantitatively determining whether at least one ferromagnetic component is missing from an assembly under inspection, comprising:

providing means for generating a magnetic field;

providing means, responsive to said means for generating, for producing an output signal wherein said step of providing said means for producing includes the step of reducing the amount of force exerted on said means for producing including reducing the amount of force exerted by said means for generating on said means for producing wherein sensitivity of said means for producing is improved;

providing processing means responsive to said means for producing;

establishing at least one reference ferromagnetic related value;

storing said reference ferromagnetic related value;

positioning an assembly for inspection relative to said means for generating, wherein the assembly has, under normal conditions, at least one component having ferromagnetic material;

obtaining said output signal from said means for producing after said positioning step, said output signal being a quantitative representation of one of the absence and the presence of said at least one ferromagnetic component;

determining whether said at lest one ferromagnetic component is missing from the inspected assembly using said reference ferromagnetic related value and said output signal; and outputting an indication of whether said at least one ferromagnetic component is missing from the inspected assembly using said processing means.

11. A method, as claimed in claim 10, wherein:

said step of providing said means for producing includes preventing excessive negative loading of said means for producing.

12. An apparatus for quantitatively determining whether at least one of two ferromagnetic components is missing from an assembly, comprising:

means for supporting an assembly for inspection in which the assembly, under normal conditions, has at least two ferromagnetic components;

means for generating a magnetic field in which the assembly is adapted to be disposed within the magnetic field, a portion of said means for generating being adapted to be physically displaced in response to a force applied thereto;

means, responsive to physical displacement of said portion of said means for generating, for producing an output signal quantitatively relating to one of the presence and absence of said at least one of said two ferromagnetic components of the assembly for inspection; and processing means responsive to said output signal from said means for producing for quantitatively determining a ferromagnetic related magnitude relating to said output signal, said processing means including means for storing a reference ferromagnetic related value wherein said reference ferromagnetic related value and said ferromagnetic related magnitude are used in determining whether said at least one of said two ferromagnetic components is missing from the inspected assembly and wherein, if said at least one of said two ferromagnetic components is missing, said reference ferromagnetic related value and said ferromagnetic related magnitude are used to determine which of said at least one of said two ferromagnetic components is missing from the inspected assembly.

13. An apparatus, as claimed in claim 12, wherein:

said means for generating includes magnet means and support means, with said support means being disposed between said magnet means and said means for producing.

14. An apparatus for quantitatively determining whether at least one ferromagnetic component is missing from an assembly, comprising:

means for supporting an assembly for inspection in which the assembly, under normal conditions, has at least one ferromagnetic component;

means for generating a magnetic field in which the assembly is adapted to be disposed within the magnetic field;

means responsive to said means for generating for producing an output signal quantitatively relating to one of the presence and absence of said at least one ferromagnetic component of the assembly for inspection, said means for producing including a load cell; and processing means responsive to said output signal from said means for producing for quantitatively determining a ferromagnetic related magnitude relating to said output signal, said processing means including means for storing a reference ferromagnetic related value and wherein said reference ferromagnetic related value and said ferromagnetic related magnitude are used in determining whether said at least one ferromagnetic component is missing from the inspected assembly.

15. An apparatus, as claimed in claim 14, wherein:

said means for generating includes magnet means and support means, with said support means being disposed between said magnet means and said means for producing; and wherein said apparatus includes means, connected to said support means, for reducing the amount of force exerted on said load cell.

16. An apparatus, as claimed in claim 15, wherein:

said means for reducing the amount of force includes first and second magnets wherein like poles of said magnets face each other so that a repulsion force exists therebetween tending to keep them apart.

17. An apparatus, as claimed in claim 15, further including:

means, connected to said means for reducing the amount of force, for preventing excessive negative loading of said load cell.

18. An apparatus, as claimed in claim 17, wherein:

said means for preventing includes means for engaging said means for generating a magnetic field, said means for preventing including adjusting means for preventing movement of at least portions of said means for generating.

19. An apparatus for quantitatively determining whether at least one ferromagnetic component is missing from an assembly, comprising:

means for supporting an assembly for inspection in which the assembly, under normal conditions, has at least one ferromagnetic component;

means for generating a magnetic field in which the assembly is adapted to be disposed within the magnetic field said means for generating including magnet means and support means, said magnet means and said support means being adapted to be physically displaced in response to a force applied thereto, and wherein said magnet means includes permanent magnet means;

means, responsive to physical displacement of said magnet means and said support means, for producing an output signal quantitatively relating to said at least one ferromagnetic component of the assembly for inspection, said supports means being disposed between said magnet and said means for producing; and processing means, responsive to said output signal from said means for producing, for quantitatively determining a ferromagnetic related magnitude relating to said output signal, said processing means including means for storing a reference ferromagnetic related value and wherein said reference ferromagnetic related value and said ferromagnetic related magnitude are used in determining whether said at least one ferromagnetic component is missing from the inspected assembly.

20. An apparatus, as claimed in claim 12, wherein:
said reference ferromagnetic related value is representative of al of the ferromagnetic components in the assembly.

21. An apparatus, as claimed in claim 12, wherein:
said processing means includes keyboard means and means for providing a display of information relating to said at least one ferromagnetic component of the inspected assembly.

22. An apparatus, as claimed in claim 12, wherein:
said processing means includes means for converting said output signal from said means for producing to a digital signal.

23. A method, as claimed in claim 1, wherein:
said positioning step includes maintaining the assembly for inspection in a stationary position during the inspection of the assembly.

* * * * *